US00PP35212P2

(12) United States Plant Patent
Burnett et al.

(10) Patent No.: US PP35,212 P2
(45) Date of Patent: Jun. 6, 2023

(54) ***ATHYRIUM* PLANT NAMED 'JA1966'**

(50) Latin Name: ***Athyrium* spp.**
Varietal Denomination: JA1966

(71) Applicant: Casa Flora, Inc., Dallas, TX (US)

(72) Inventors: Naud Burnett, Dallas, TX (US); Jose Aguirre, Dallas, TX (US)

(73) Assignee: Casa Flora, Inc., Dallas, TX (US)

( * ) Notice: Subject to any disclaimer, the term of this patent is extended or adjusted under 35 U.S.C. 154(b) by 0 days.

(21) Appl. No.: 17/903,485

(22) Filed: Sep. 6, 2022

(51) Int. Cl.
*A01H 9/00* (2006.01)
*A01H 6/00* (2018.01)

(52) U.S. Cl.
USPC ..... Plt./379
CPC ..... *A01H 6/00* (2018.05)

(58) Field of Classification Search
USPC ..... Plt./379
CPC ..... A01H 9/00
See application file for complete search history.

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

A new and distinct fern variety, referred to by its cultivar name, 'JA1966', is disclosed. The new variety is a distinct sterile hybrid mutation of the 'Ghost' variety characterized by exceptional grey-green colored, vertical new fronds that change color to black with arching fronds as the leaf ages. The new variety displays a stark contrast of its immature grey-green colored fronds with its mature black colored fronds.

8 Drawing Sheets

Figure 1:
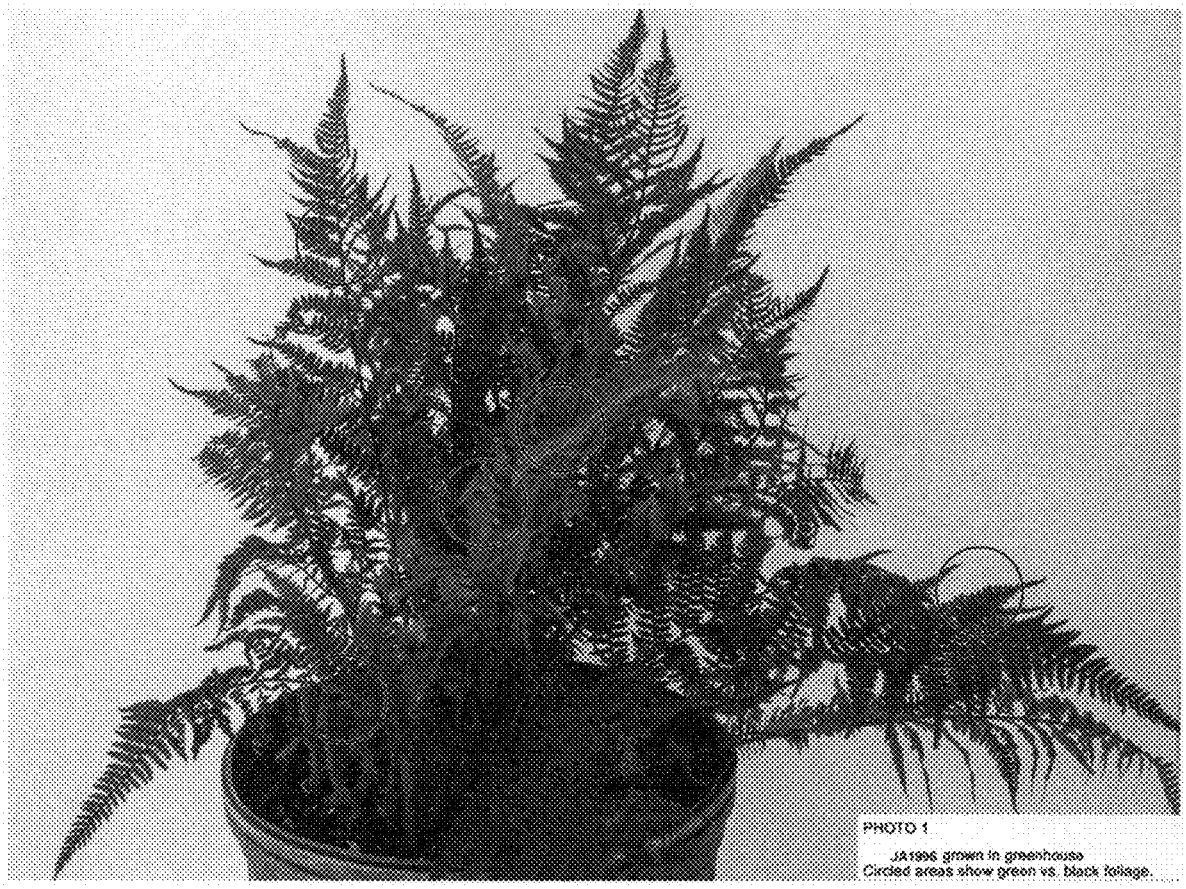

Latin name of genus and species of plant claimed: *Athyrium* spp.

Variety denomination: 'JA1966'.

BACKGROUND OF THE INVENTION

The new variety of *Athyrium* plant of the present invention is a new, distinct and sterile hybrid that arose as a chance mutated foundling (sport) that was identified in Dallas, Tex. The parent of the new variety was the 'Ghost' variety (not patented). The parent variety was propagated by tissue culture and then transplanted to cell trays. The new variety was discovered in 2013 among thousands of 'Ghost' plugs growing at a facility in Dallas, Tex. The new variety was identified due to its distinct black fronds that differed from all of the other 'Ghost' plants that were cultivated in the same round of tissue culture.

The new variety has been found to undergo asexual propagation in Dallas, Tex. by tissue culture since Aug. 5, 2020. Asexual propagation by tissue culture in Dallas, Tex. has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of *Athyrium* plant of the present invention possesses the following combination of characteristics:

(a) forms new erect fronds of glowing grey-green colored foliage that gradually change to arching and black colored with a unique contrast of color,
(b) is sterile, and
(c) exhibits no stems above ground.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'Ghost' variety (i.e., the parent variety) produces mature fronds that are upright and remain the same color as the immature fronds which is near Greyed-Green Group 191B, whereas the new variety produces mature fronds that begin to arch and transition to black colored fronds commonly near Black Group 202A, creating an intermixed mature and immature frond coloring on the new variety plant. Moreover, the new variety can be readily distinguished from other similar non-parental varieties. For example, the 'Pewter Lace' variety (U.S. Plant Pat. No. 15,721) produces a pewter tone to the leaves, silver over grey green, and this color persists from new growth to mature; whereas the new variety produces new erect fronds of glowing grey-green colored foliage that gradually change to black colored of the mature foliage.

The new variety has been named 'JA1966'. The trademark name for the new variety is DARK STAR™.

The new variety has not been sold or offered for sale as of August 2022.

BRIEF DESCRIPTION OF THE PHOTOGRAPH

The accompanying photographs of the drawings show as nearly true as it is reasonably possible to make the same, in a color illustration of this character, typical specimens of plants of the new variety and that of the parent variety. The *Athyrium* plants of the new variety and the parent variety were approximately three years of age and were observed growing in 2-gallon containers at a greenhouse in Dallas, Tex.

FIG. 1—illustrates a specimen of the new variety; circled areas show green versus black colored foliage.

Figure 2:
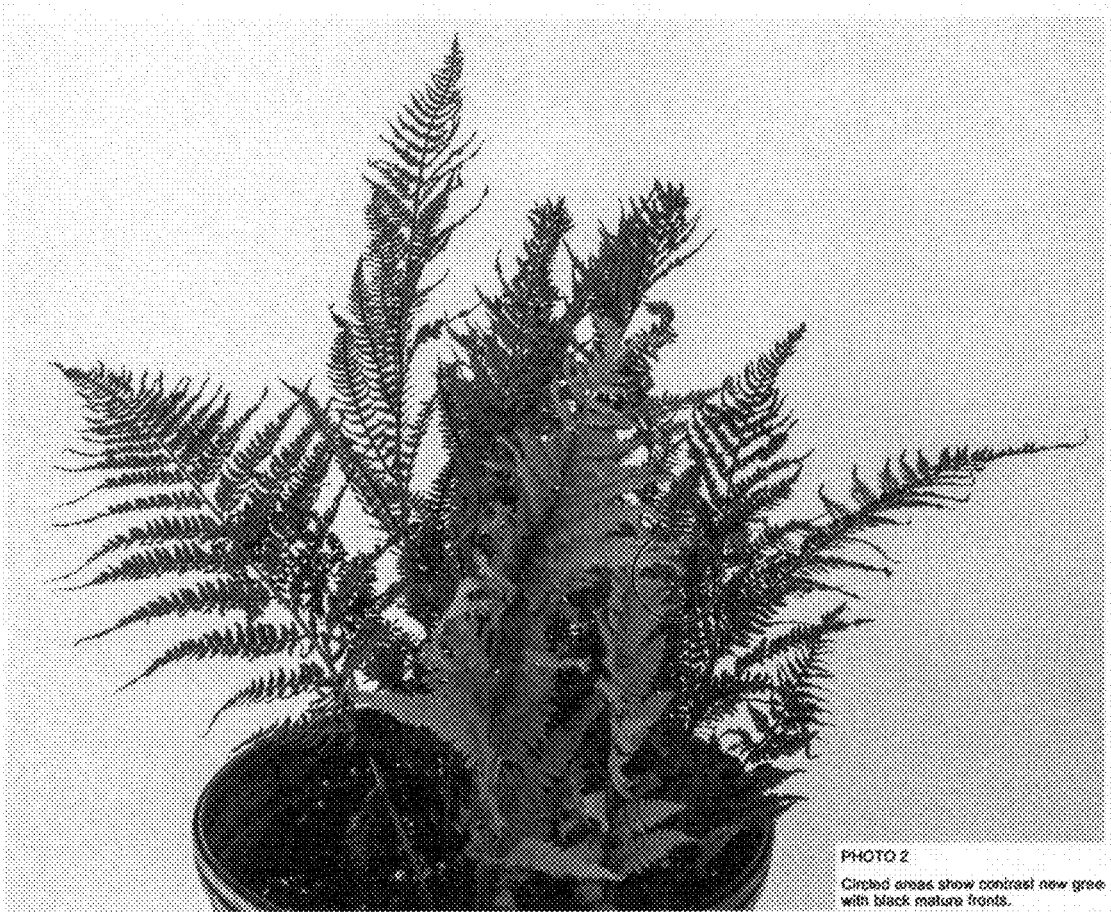

FIG. 2—illustrates a specimen of the new variety; circle area shows contrast of new green colored fronds with black colored mature fonds.

Figure 3:
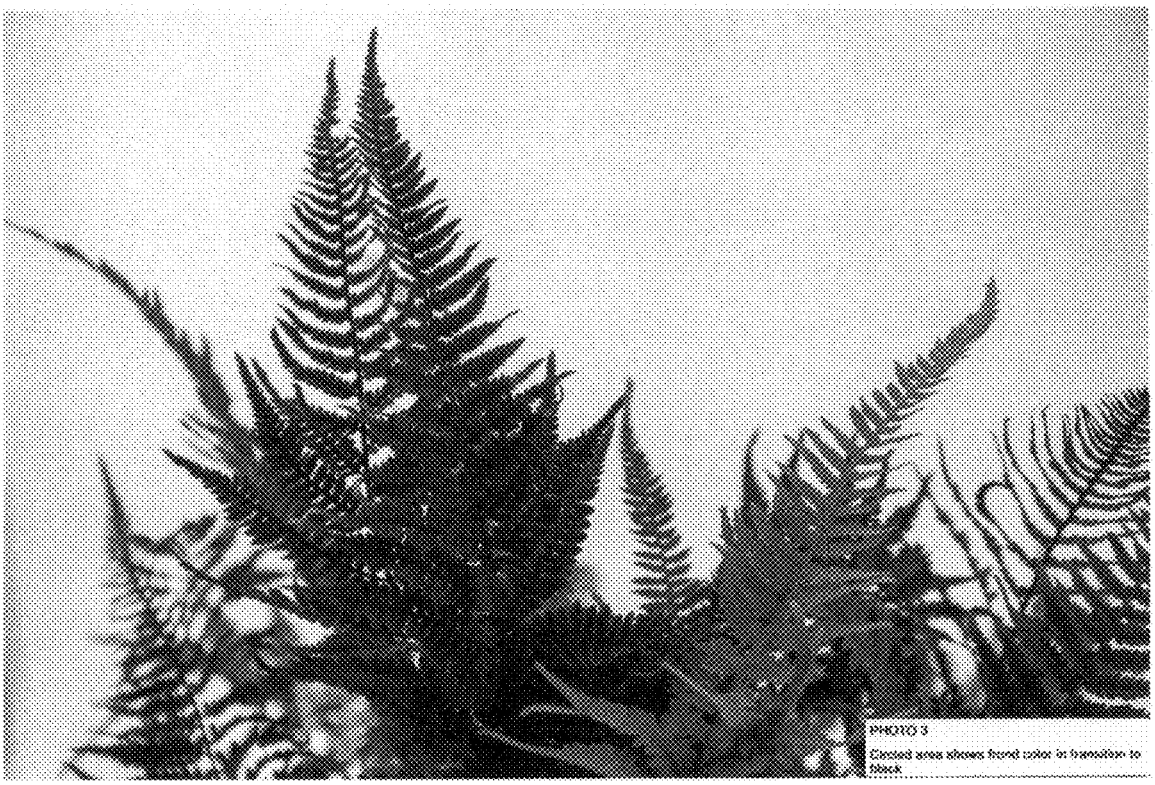

FIG. 3—illustrates a specimen of the new variety; circled area shows frond color in transition to black.

Figure 4:
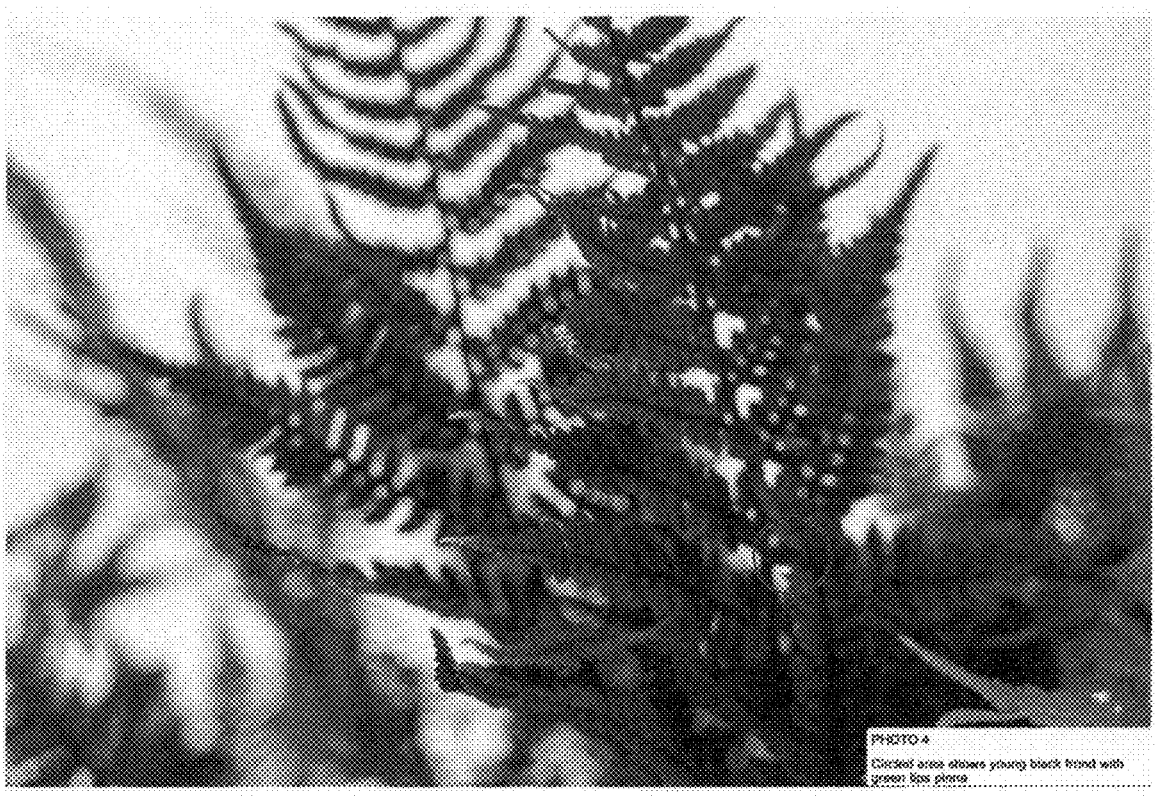

FIG. 4—illustrates a specimen of the new variety; circled area indicates a young black colored frond with green colored tips pinna.

Figure 5:
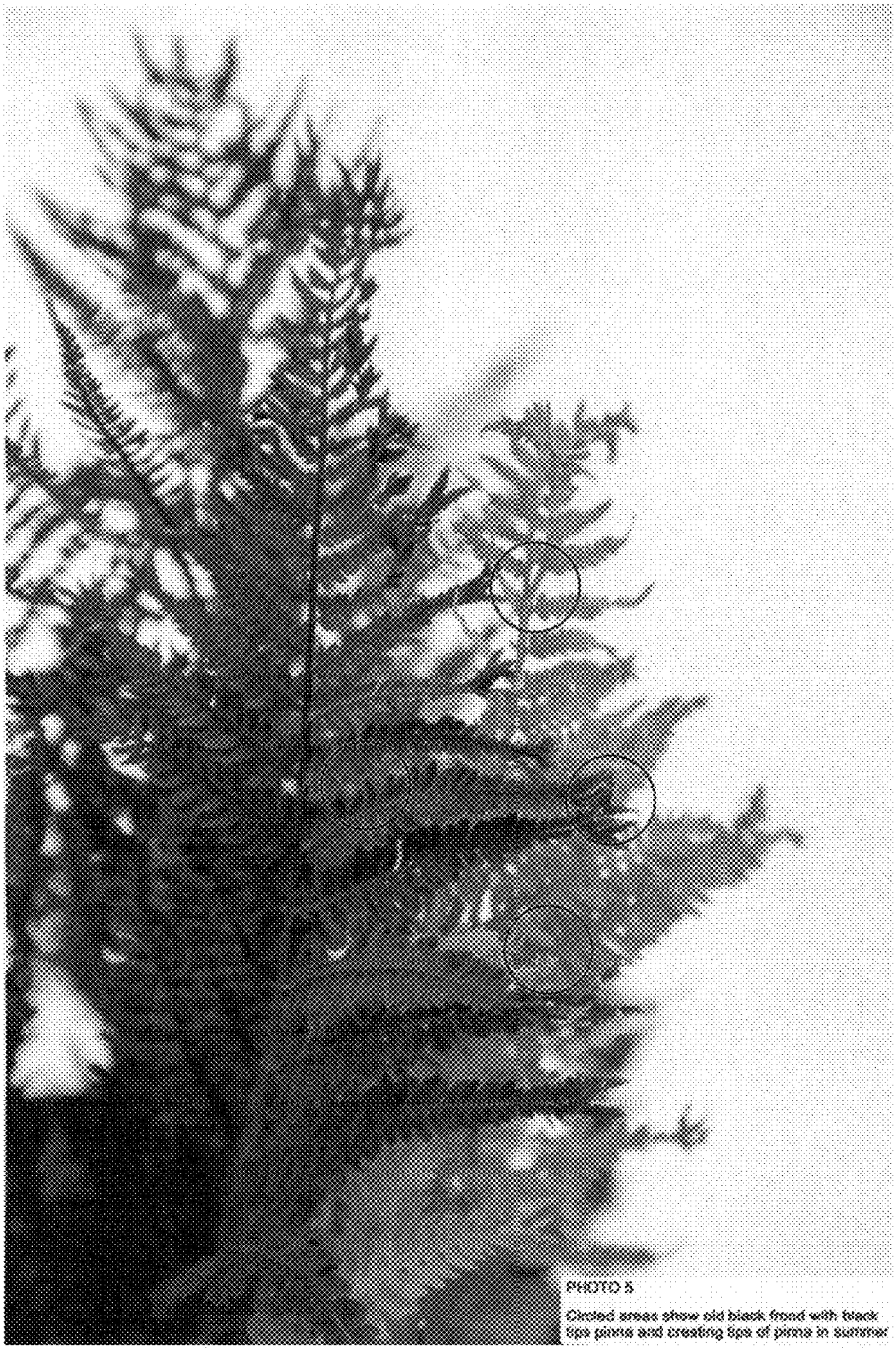

FIG. 5—illustrates a specimen of the new variety; circled areas show old black colored frond with black colored tips pinna and cresting tips of pinna in summer.

Figure 6:
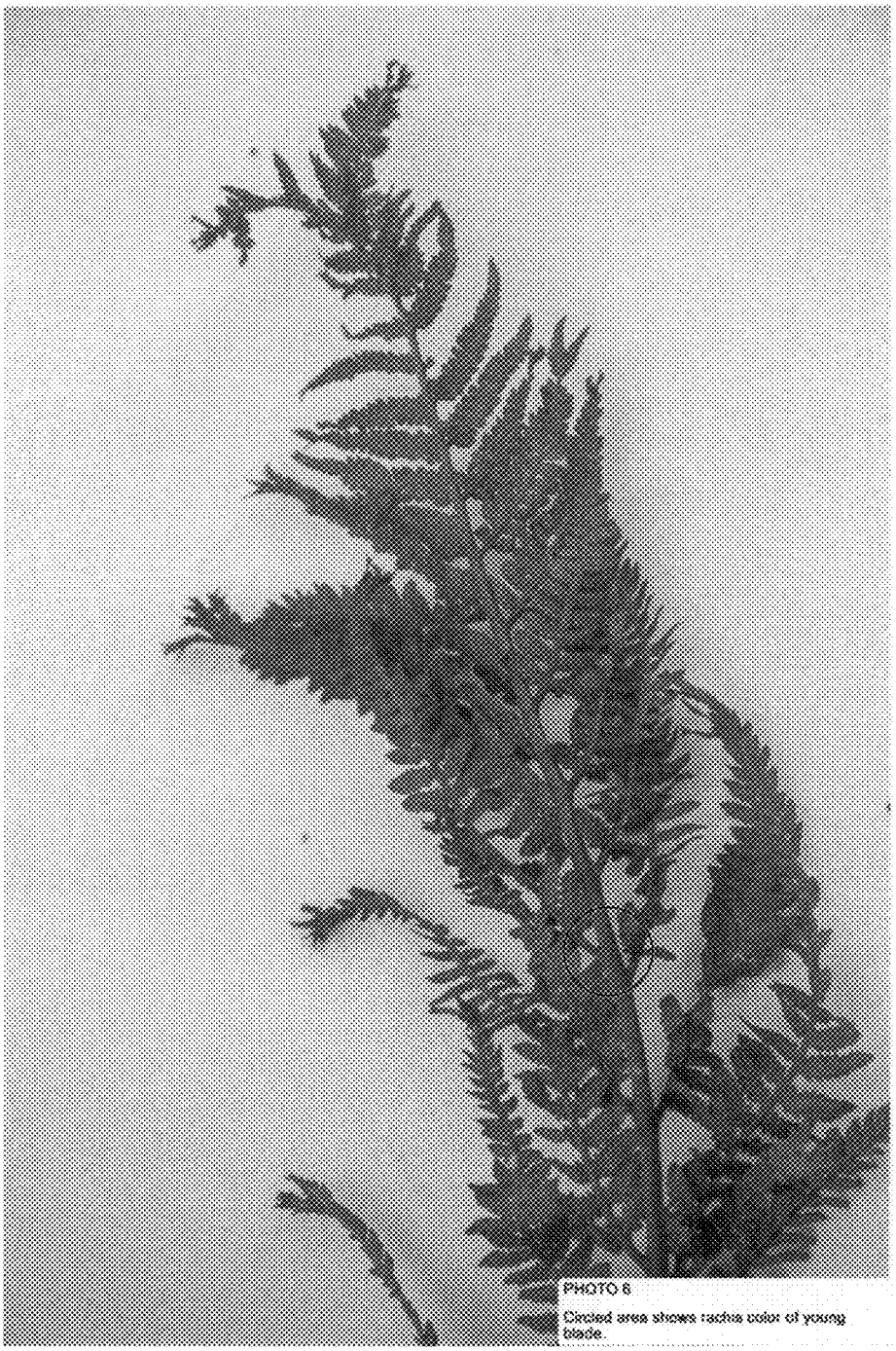

FIG. 6—illustrates a specimen of young blade of the new variety; circled area shows rachis of young blade.

Figure 7:
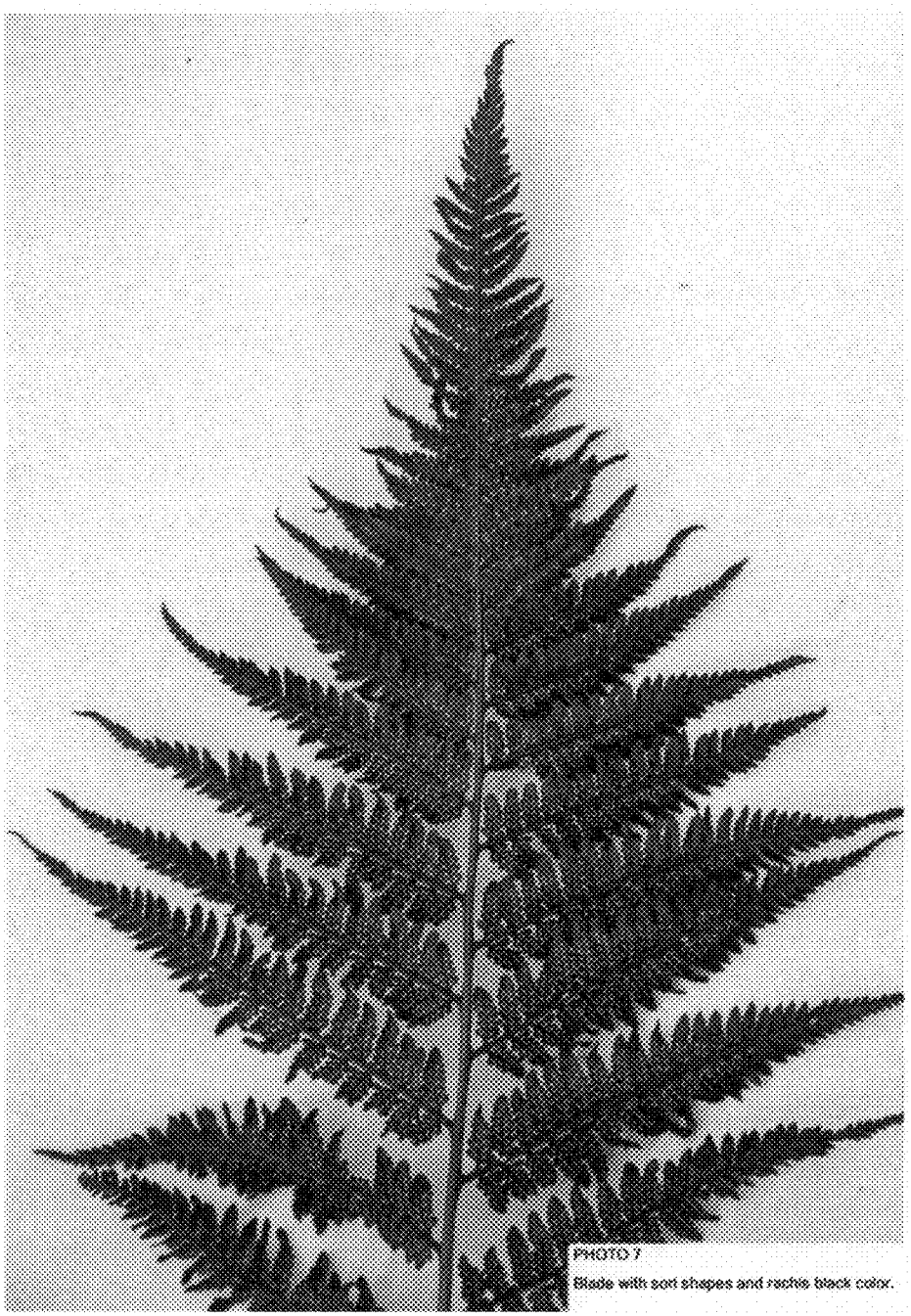

FIG. 7—illustrates a specimen of the new variety—blade black in color, with sori shapes and rachis.

Figure 8:
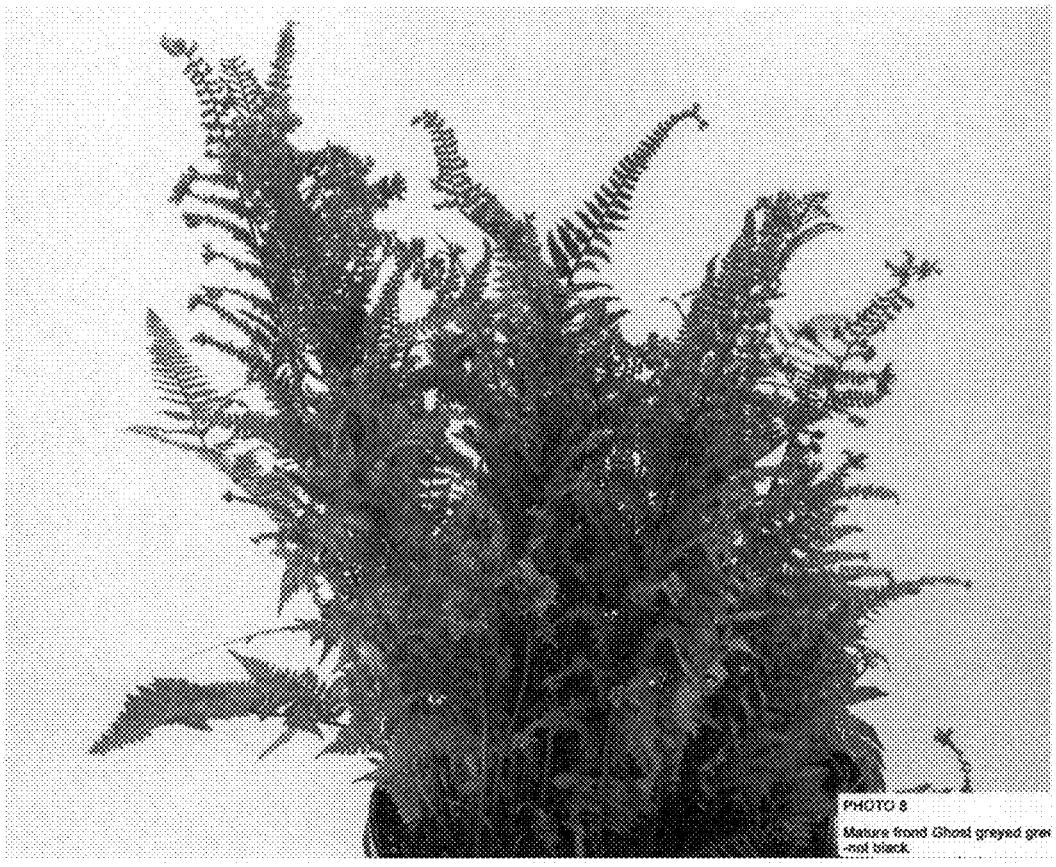

FIG. 8—illustrates a mature specimen of the 'Ghost' variety (i.e., the parent variety)

DETAILED BOTANICAL DESCRIPTION

The chart used in the identification of the colors is that of The Royal Horticultural Society Colour Chart (The R.H.S. Colour Chart, 2001 edition), London, England. The terminology which precedes reference to the chart has been added to indicate the corresponding color in more common terms. The description is based on the observation of three-year-old specimens grown in two-gallon containers in a heated and cell-pad water cooler equipped greenhouse in Dallas, Tex. during August 2022. The observed specimens are from tissue culture of the original mutant foundling and were transplanted first to 72-cell trays and then repotted in several stages to a 2-gallon container over the course of three years. Tissue culture was completed in a laboratory and transplanted/potted plant were grown in a heated and cell-pad water cooler equipped greenhouse. The entire process took place in Dallas, Tex.

Botanical classification: *Athyrium* spp. cultivar JA1966.

Commercial classification: *Athyrium* Plant.

Plant:

*Habit*.—Clumping and upright; as the plant fronds mature the outer frond flex into an arching form to create a broader appearance.

*Height*.—Approximately 18-24 inches on average.

*Width*.—Approximately 18 inches on average.

*Form*.—Terrestrial, rhizomatous fern.

*Root*.—Rhizomatous.

*Stem*.—None above ground, rhizomatous are short.

Foliage:

*Type*.—Compound.

*Number of fronds*.—More than 20.

*Pinna*.—Shape is lanceolate, twice pinnate pinnule is lanceolate to oblong; length is 12.5 cm on average for the third pinna from the bottom; width is 2.5 cm on average; and apex is acute.

*Frond color*.—Both upper and lower surfaces young fronds are a vibrant grey-green color, commonly near Grey-Green Group 191B. Both upper and lower surfaces of maturing fronds turn a blend of colors as they transition from a color near Grey-Green Group 191B to their final, mature color of near Black Group 202A. Plants remain a color near Black Group 202A until the winter season, when they go into dormancy; tips of pinna remain a color near Grey-Green Group 191B longer and gradually turn a color near Black Group 202A.

*Blade length*.—Approximately 40 cm on average.

*Frond size*.—Width is approximately 14 cm on average; height approximately 53.8 cm.

*Margins*.—2 pinnate; pinnule is lobed and incised.

*Apex*.—Acuminate, pinnatifid.

*Base*.—Round to truncate.

*Texture*.—Upper surface is glabrous and lower surface is bumpy due to sori.

*Pinnule*.—Apex is acute; length is approximately 1.2 cm on average; and width is approximately 2.0 cm on average.

*Pinna rachis*.—Grooved; length is approximately 11.0 cm on average, width is approximately 0.5 mm; and texture is glabrous.

*Blade rachis color*.—Immature growth is commonly near Greyed-Green Group 191B; as growth matures transitions to near Greyed-Purple Group 186A intermixed with about 50% blotches of near Black Group 202A.

*Blade rachis texture*.—Multicellular hairs on rachis V groove on rachis not continuous to pinna but disconnected from pinna V groove.

*Blade rachis*.—Grooved; length is approximately 40.0 cm on average; width is approximately 2.0 mm on average 6.5 cm from apex of blade.

*Venation*.—Color is commonly near Greyed-Green Group 191B on young leaves; venation color slowly transition as the plant matures to intermediate grey tones and finally to near Black Group 202A when fronds become black; pattern is pinnate.

*Petiole* (*stipe*).—Texture is glabrous with chaffy scales which are commonly near Greyed-Orange Group 167A that are mainly at the base but occasionally elsewhere; color is commonly near Greyed-Purple Group 186A; grooved; length is approximately 13.8 cm; and width is approximately 1.4 cm on average.

Fruiting body:

*Type*.—Sporangium; all fronds have sori.

*Fertility*.—Sterile.

*Sori*.—Size: length is approximately 0.1 mm and width is approximately 0.02 mm. — color: commonly near Yellow-Green Group 150C. — shape: covered with indusium; most are elongated, opening on the edge that is facing the edge of the pinna, although it is common for some to be slightly curved into a J or C shape, a trait similar to those observed on the parent variety 'Ghost'. — location: dorsal, on every pinnule at the tip of the vein.

Development:

*USDA hardiness zone*.—Zones 6-9 and possibly colder to zone 2.

*Tolerance to disease*.—To date no diseases have been observed.

*Pest resistance/susceptibility*.—To date no susceptibility to pests has been observed.

The new 'JA1966' variety has not been observed under all possible environmental conditions to date. Accordingly, it is possible that the phenotypic expression may vary somewhat with changes in light intensity and duration, cultural practices, and other environmental conditions.

We claim:

1. A new and distinct variety of *Athyrium* plant named 'JA1966' characterized by the following combination of characteristics:

(a) forms new erect fronds of glowing grey-green colored foliage that gradually change to arching and black colored with a unique contrast of color, (b) is sterile, and (c) exhibits no stems above ground;

substantially as herein shown and described.

* * * * *

PHOTO 5

Circled areas show old black frond with black tips pinna and creating tips of pinna in summer

PHOTO 6

Circled area shows rachis color of young blade.